United States Patent [19]

Petersen et al.

[11] Patent Number: 4,559,341

[45] Date of Patent: Dec. 17, 1985

[54] QUINOLONECARBOXYLIC ACIDS AND ANTIBACTERIAL AGENTS CONTAINING THESE COMPOUNDS

[75] Inventors: Uwe Petersen, Leverkusen; Klaus Grohe, Odenthal; Engelbert Kühle, Bergisch-Gladbach; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 576,595

[22] Filed: Feb. 3, 1984

[30] Foreign Application Priority Data

Feb. 25, 1983 [DE] Fed. Rep. of Germany ....... 3306771

[51] Int. Cl.$^4$ ................. A61K 31/495; C07D 401/04; C07D 401/14
[52] U.S. Cl. .................................... 514/254; 544/358; 544/363; 546/156
[58] Field of Search ........................ 544/363; 424/250; 514/254

[56] References Cited

U.S. PATENT DOCUMENTS 3,149,104  9/1964  Lesher et al. ..................... 546/156

FOREIGN PATENT DOCUMENTS

| 2939783 | 4/1980 | Fed. Rep. of Germany | 544/363 |
| 3306771 | 8/1984 | Fed. Rep. of Germany | 544/363 |
| 3306772 | 8/1984 | Fed. Rep. of Germany | 544/363 |
| 2085875 | 5/1982 | United Kingdom | 544/363 |

*Primary Examiner*—Glennon H. Hollrah
*Assistant Examiner*—James H. Turnipseed
*Attorney, Agent, or Firm*—Sprung Horn Kramer & Woods

[57] ABSTRACT

The invention relates to quinolone carboxylic acids, pharmaceutical compositions containing said quinolone carboxylic acids and the use of said compounds and compositions for treatment of bacterial infection. Also included in the invention are process for the manufacture of the active quinolone carboxylic acids.

15 Claims, No Drawings

QUINOLONECARBOXYLIC ACIDS AND ANTIBACTERIAL AGENTS CONTAINING THESE COMPOUNDS

The present invention relates to quinolonecarboxylic acids, processes for their preparation and antibacterial agents containing these compounds.

It has been found that the new quinolonecarboxylic acids of the formula (I)

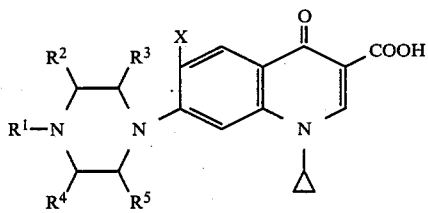

in which
R¹ represents a radical CO—R⁶, CN, SO₂—R⁷ or S—R⁸,
wherein
R⁶ denotes hydrogen, optionally substituted straight-chain or branched alkyl having 1 to 6 carbon atoms, optionally substituted aryl having 6 or 10 carbon atoms, optionally substituted aralkyl having 6 carbon atoms, in the aryl part and 1 to 3 carbon atoms in the alkyl part, optionally substituted alkoxy or alkylthio having 1 to 6 carbon atoms, optionally substituted aryloxy having 6 carbon atoms, optionally substituted benzyloxy, amino, optionally substituted alkylamino or dialkylamino having 1 to 6 carbon atoms in the alkyl radical or optionally substituted phenylamino and
R⁷ denotes optionally substituted straight-chain or branched alkyl having 1 to 5 carbon atoms, phenyl or methylphenyl and
R⁸ denotes methoxycarbonyl, trichloromethyl, trifluoromethyl or dichlorofluoromethyl,
R², R³, R⁴ and R⁵ can be identical or different and represent hydrogen, methyl, ethyl, n- or i-propyl, and
X represents hydrogen, halogen, preferably fluorine or chlorine, or nitro,
and their pharmaceutically usable acid addition salts, alkali metal salts and alkaline earth metal salts and hydrates possess a good antibacterial acttion against both gram-positive and gram-negative bacteria.

As used herein and unless otherwise specified, the terms "aryl", "arallyl" and "aryloxy" define aromatic moieties which are mono- or bi-cyclic carbocyclic, such as phenyl, naphthyl and biphenyl.

Preferred compounds are those of the formula (I) in which the symbols have the following meanings:
R¹=CO-R⁶, CN, SO₂-R⁷, S-R⁸;
R⁶=hydrogen, straight-chain or branched alkyl which has 1 to 5 C atoms and is optionally substituted by 1 to 3 substituents from the series comprising amino, chlorine, alkoxycarbonyl having 1 to 4 carbon atoms in the alkyl part, carboxyl, alkoxy having 1 to 4 carbon atoms, hydroxyl and trifluoromethylthio, phenyl which is optionally substituted by 1 to 5 (preferably 1, 2 or 3) substituents from the series comprising fluorine, chlorine, hydroxyl, methoxy, amino and carboxyl, benzyl which is optionally substituted by amino, alkoxy or alkylthio which has 1 to 5 C atoms and is optionally substituted by fluorine, chlorine, pyrazol-1-yl, 1,2,3-triazol-1-yl or N-oxido-2-, -3- or -4-pyridyl-methyl, benzyloxy, amino, alkylamino which has 1 to 5 C atoms and is optionally substituted by alkoxycarbonyl having 1 to 3 C atoms in the alkyl part or by benzyloxycarbonyl or carboxyl, or phenylamino,
R⁷=straight-chain or branched alkyl which has 1 to 4 C atoms and is optionally substituted by 1 to 3 substituents from the series comprising fluorine and amino, or phenyl or methylphenyl,
R⁸=methoxycarbonyl, trichloromethyl or dichlorofluoromethyl,
R², R³, R⁴ and R⁵=hydrogen, methyl or ethyl and
X=hydrogen, fluorine, chlorine or nitro.

Particularly preferred compounds are those of the formula (I) in which the symbols have the following meanings:
R¹=CO-R⁶, CN, SO₂R⁷, S-R⁸,
R⁶=hydrogen, straight-chain or branched alkyl which has 1 to 4 C atoms and which is optionally substituted by 1 or 2 substituents from the series comprising amino, alkoxycarbonyl having 1 to 3 carbon atoms in the alkyl part, carboxyl, alkoxy having 1 to 3 carbon atoms and trifluoromethylthio, phenyl which is optionally substituted by 1 to 5 substituents from the series comprising chlorine, hydroxyl, amino and carboxyl, benzyl which is optionally substituted by amino, alkoxy which has 1 to 4 C atoms and is optionally substituted by pyrazol-1-yl, 1,2,3-triazol-1-yl, N-oxido-2-, -3- or -4-pyridylmethyl, alkylthio having 1 to 2 C atoms, benzyloxy, amino, or alkylamino which has 1 to 5 C atoms and is optionally substituted by alkoxycarbonyl having 1 to 3 C atoms in the alkyl part or by carboxyl,
R⁷=straight-chain or branched alkyl having 1 to 3 C atoms, phenyl or methylphenyl,
R⁸=methoxycarbonyl, trichloromethyl or dichlorofluoromethyl,
R²=hydrogen, methyl or ethyl,
R³=hydrogen,
R⁴=hydrogen, or methyl,
R⁵=hydrogen and
X=hydrogen, fluorine, chlorine or nitro.

Furthermore, it has been found that the compounds according to the invention, of the formula (I), are obtained when a compound of the formula (II)

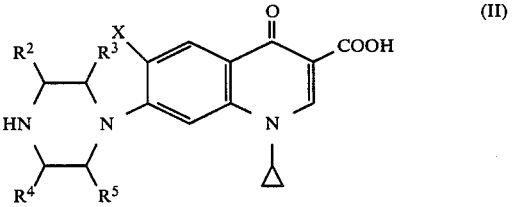

in which
X, R², R³, R⁴ and R⁵ have the meanings given above, is reacted with a compound of the formula (III)

R₁-Y (III)

in which
R¹ has the meaning given above and
Y represents a leaving group, such as halogen, preferably chlorine, fluorine or bromine, methoxy, ethoxy, phenoxy, 4-nitrophenoxy, 2,3,5-trichlorophenoxy or alkoxycarbonyloxy, (Method A).

The compounds according to the invention, of the formula (I), are also obtained when compounds of the formula (II)

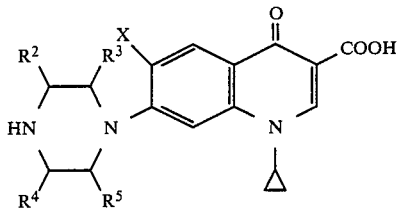
(II)

are reacted with isocyanates of the formula (IV)

R'-NCO
(IV)
in which
R' denotes optionally substituted alkyl or phenyl, to give the compounds according to the invention, of the formula (Ia)=(I; R$^1$=CO—NH—R') (method B).

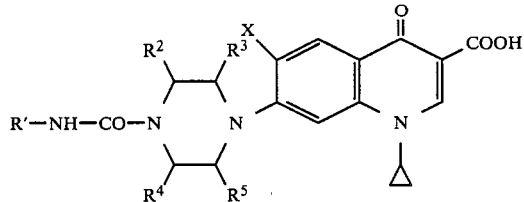
(Ia)

The compounds according to the invention, of the formula (I) are also obtained when compounds of the formula (II)

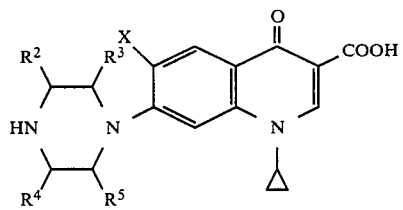
(II)

are reacted with anhydrides of the formula (V)

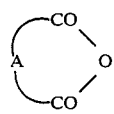
(V)

in which
A denotes an optionally substituted alkylene chain having 2 or 3 carbon atoms or an arylene radical, to give the compounds according to the invention, of the formula (Ib)=(I; R$^1$=CO-A-COOH) (method C).

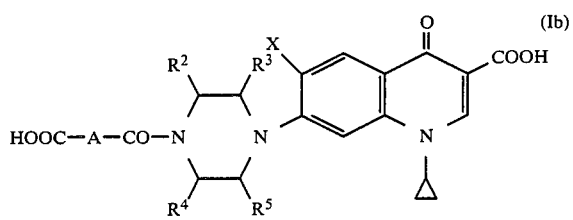
(Ib)

Surprisingly, the quinolonecarboxylic acids according to the invention have a substantially greater antibacterial action than the known 1-ethyl-6-fluoro-1,4-dihydro-4-oxo-7-(piperazin-1-yl)-quinoline-3-carboxylic acid (norfloxacin). The substances according to the invention thus represent an enrichment of pharmacy.

If, for example, 1-cyclopropyl-6-fluoro-1,4-dihydro-4-oxo-7-(piperazin-1-yl)-quinoline-3-carboxylic acid and propionic acid anhydride are used as starting compounds in the reaction of (II) with (III) according to method A, the course of the reaction can be represented by the following equation:

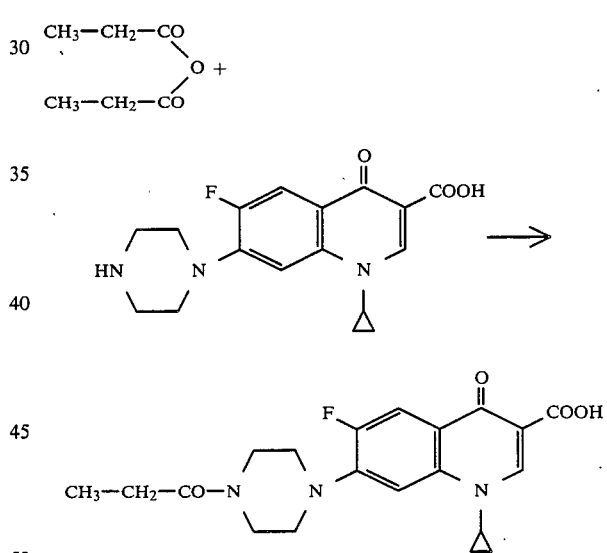

If, for example, 1-cyclopropyl-6-fluoro-1,4-dihydro-4-oxo-7-(piperazin-1-yl)-quinoline-3-carboxylic acid and methyl isocyanate are used as starting substances in the reaction of (II) with (IV) according to method B, the course of the reaction can be represented by the following equation.

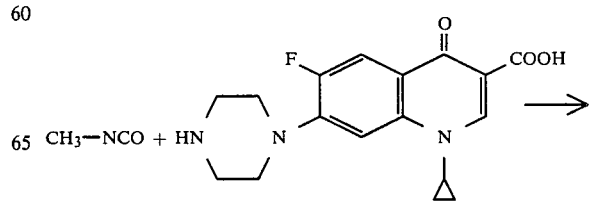

-continued

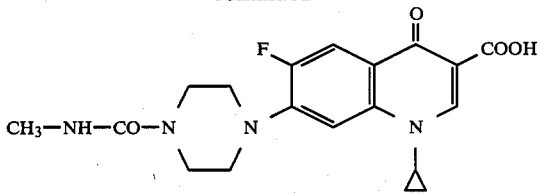

If, for example, 1-cyclopropyl-6-fluoro-1,4-dihydro-4-oxo-7-(piperazin-1-yl)-quinoline-3-carboxylic acid and glutaric acid anhydride are used as starting compounds in the reaction of (II) with (V) according to method C, the course of the reaction can be represented by the following equation:

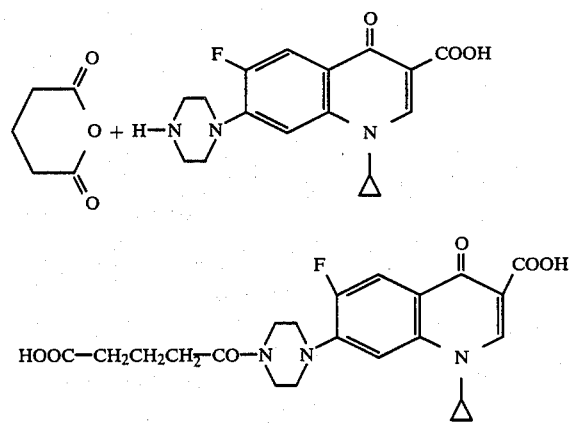

The compounds of the formula (II) which are used as starting compounds can be prepared by reacting compounds of the formula (VI)

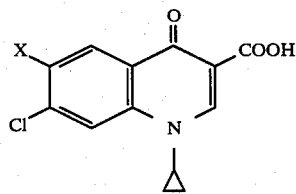

with piperazine or piperazine derivatives of the formula (VII)

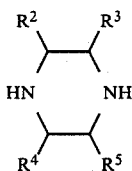

The reaction is carried out in a diluent, such as dimethylsulphoxide, hexamethylphosphoric acid triamide, sulpholane, water, an alcohol or pyridine, at temperatures of 20°–200° C., preferably at 80°–180° C. In carrying out the process, 1–15 mol of the compound VII, preferably 1–6 mol of the compound VII, are employed per mol of carboxylic acid VI. Where equivalent amounts of the carboxylic acid VI and of the piperazine derivative VII are used, the reaction is carried out in the presence of an acid-binding agent, for example triethylamine, 1,4-diazabicyclo-[2.2.2]-octane or 1,8-diaza-bicyclo[5.4.0]undec-7-ene.

The following may be mentioned as examples of the starting materials of the formula (II) which can be prepared in this manner:

1-cyclopropyl-6-fluoro-1,4-dihydro-4-oxo-7-(piperazin-1-yl)-quinoline-3-carboxylic acid,
1-cyclopropyl-6-fluoro-1,4-dihydro-4-oxo-7-(2,5-dimethylpiperazin-1-yl)-quinoline-3-carboxylic acid,
1-cyclopropyl-6-fluoro-1,4-dihydro-4-oxo-7-(3,5-dimethylpiperazin-1-yl)-quinoline-3-carboxylic acid,
1-cyclopropyl-6-fluoro-1,4-dihydro-4-oxo-7-(3-methylpiperazin-1-yl)-quinoline-3-carboxylic acid,
1-cyclopropyl-6-fluoro-1,4-dihydro-4-oxo-7-(3-ethylpiperazin-1-yl)-quinoline-3-carboxylic acid,
1-cyclopropyl-6-fluoro-1,4-dihydro-4-oxo-7-(3,5-diethylpiperazin-1-yl)-quinoline-3-carboxylic acid,
1-cyclopropyl-6-fluoro-1,4-dihydro-4-oxo-7-(2,3,5-trimethyl-piperazin-1-yl)-quinoline-3-carboxylic acid,
1-cyclopropyl-6-fluoro-1,4-dihydro-4-oxo-7-(2,3,5,6-tetramethyl-piperazin-1-yl)-quinoline-3-carboxylic acid,
1-cyclopropyl-1,4-dihydro-4-oxo-7-(piperazin-1-yl)-quinoline-3-carboxylic acid,
1-cyclopropyl-1,4-dihydro-6-nitro-4-oxo-7-(piperazin-1-yl)-quinoline-3-carboxylic acid and
6-chloro-1-cyclopropyl-1,4-dihydro-4-oxo-7-(piperazin-1-yl)-quinoline-3-carboxylic acid.

The 7-chloro-1-cyclopropyl-6-fluoro-1,4-dihydro-4-oxo-quinoline-3-carboxylic acid of the formula VIa (VI; X=F) used as an intermediate product can be prepared in accordance with the following equation:

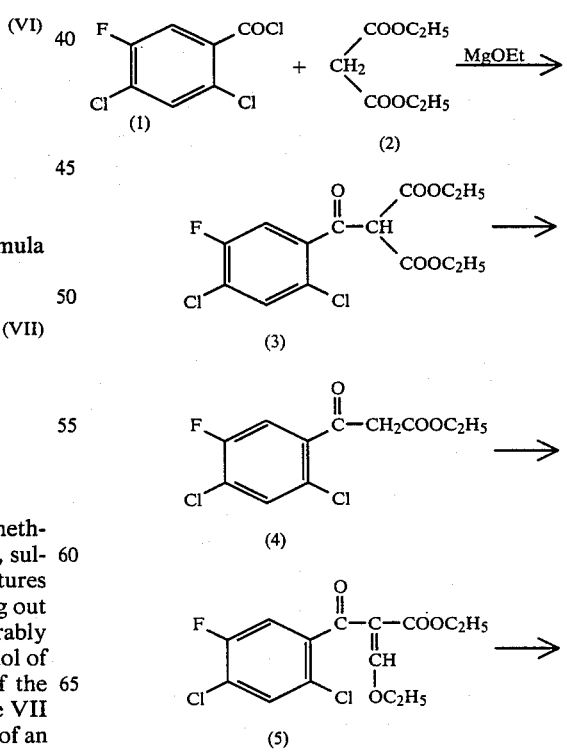

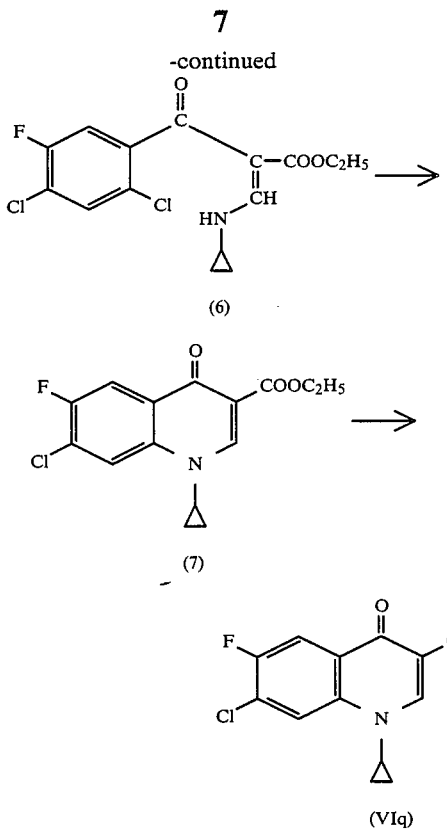

(6)

(7)

(VIq)

According to this, diethyl malonate (2) is acylated with 2,4-dichloro-5-fluoro-benzoyl chloride (1) in the presence of magnesium alcoholate to give the acyl malonate [Organikum, 3rd edition, 1964, page 483].

Partial hydrolysis and decarboxylation of (3) in an aqueous medium with catalytic amounts of p-toluenesulphonic acid gives, in good yield, the ethyl aroylacetate (4), which is converted with triethyl o-formate/acetic anhydride to the ethyl 2-(2,4-dichloro-5-fluoro-benzoyl)-3-ethoxy-acrylate (5). The reaction of (5) with cyclopropylamine in a solvent, such as, for example, methylene chloride, alcohol, chloroform, cyclohexane or toluene, takes place by means of a slightly exothermic reaction to give the desired intermediate product (6).

The cyclisation (6)→(7) is carried out in a temperature range from about 60° to 280° C., preferably 80° to 180° C.

Dioxane, dimethylsulphoxide, N-methyl-pyrrolidone, sulpholane, hexamethylphosphoric acid triamide and, preferably, N,N-dimethylformamide can be Suitable acid-binding agents for this reaction stage are potassium tert.-butanolate, butyl-lithium, lithium-phenyl, phenyl magnesium bromide, sodium methylate, sodium hydride and particularly preferably potassium carbonate or sodium carbonate. It can be advantageous to employ an excess of 10 mol% of base.

The ester hydrolysis of (7) under basic or acidic conditions, which takes place in the last step, leads to 7-chloro-1-cyclopropyl-6-fluoro-1,4-dihydro-4-oxo-quinoline-3-carboxylic acid VIa.

The 2,4-dichloro-5-fluoro-benzoyl chloride (1) used as the starting material for this synthesis route, and the corresponding carboxylic acid, as well as the 3-fluoro-4,6-dichlorotoluene (10) required for the preparation of (1), are prepared in accordance with the equation below, starting from 2,4-dichloro-5-methyl-aniline (8):

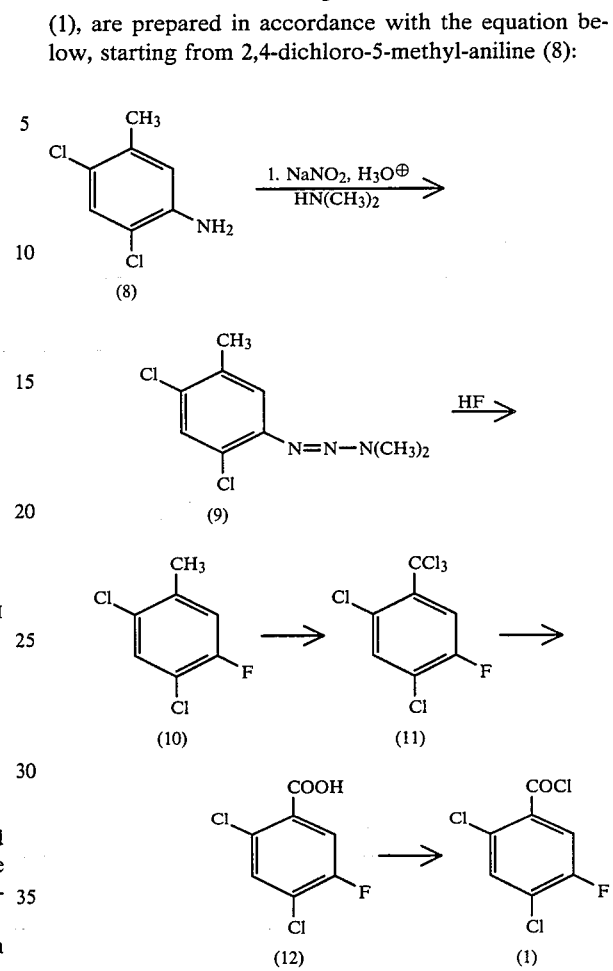

According to this, 2,4-dichloro-5-methyl-aniline (8) is diazotised with the aid of $NaNO_2$, and the resulting diazonium salt is converted with dimethylamine to the triazine (9).

The triazine (9) is dissolved in excess anhydrous HF. The triazine is thus cleaved into 2,4-dichloro-5-methyl-diazonium fluoride and dimethylamine. Without intermediate isolation, this solution is subjected to thermal cleavage at 130°–140° C., $N_2$ being split off and 3-fluoro-4,6-dichlorotoluene (10) being obtained. Yield: 77.7% of theory.

The 3-fluoro-4,6-dichlorotoluene (10) is chlorinated in a temperature range of 110°–160° C. under UV irradiation to give 2,4-dichloro-5-fluoro-1-trichloromethyl-benzene (11).

The hydrolysis of (11) with 95% strength sulphuric acid leads to 2,4-dichloro-5-fluoro-benzoic acid (12), which is converted with thionyl chloride to the carboxylic acid chloride (1) (b.p. 120°/20 mbar; $n_d^{20}$ 1.5722).

The quinolonecarboxylic acids below, which are used as intermediate products, are prepared in an analogous manner.

7-Chloro-1-cyclopropyl-1,4-dihydro-4-oxo-quinoline-3-carboxylic acid (VIb) (m.p. 308° C.) from 2,4-dichlorobenzoyl chloride (J. Chem. Soc. 83, 1,213 (1903));

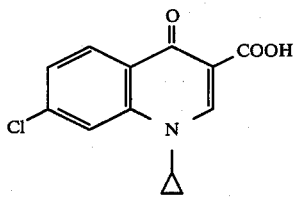

6,7-dichloro-1-cyclopropyl-1,4-dihydro-4-oxo-quinoline-3-carboxylic acid (VIc) (m.p. 265° C.) from 2,4,5-trichlorobenzoyl chloride;

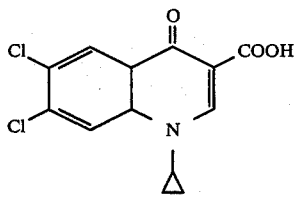

7-chloro-1-cyclopropyl-1,4-dihydro-6-nitro-4-oxo-quinoline-3-carboxylic acid (VId) (m.p. 265°–275° C. decomp.) from 2,4-dichloro-5-nitro-benzoyl chloride.

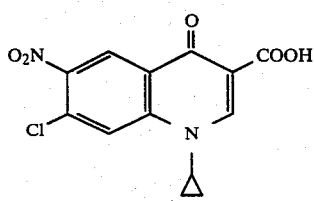

The compounds which can be used according to the invention, of the formula (III), are already known. The following may be mentioned as examples:

Formic acetic anhydride, acetic anhydride, propionic anhydride, acetyl chloride, chloroacetyl chloride, dichloroacetyl chloride, bromoacetyl bromide, butyryl chloride, 4-chlorobutyl chloride, isobutyryl chloride, 3-methylbutyryl chloride, pentanoyl chloride, benzoyl chloride, 3-chlorobenzoyl chloride, 4-fluorobenzoyl chloride, 4-nitrobenzoyl chloride, 2-chloro-4-nitrobenzoyl chloride, 4-methylbenzoyl chloride, monomethyl chloroformyl succinate, trifluoromethylthioacetic fluoride, 4-nitrophenyl N-(tert.-butoxycarbonyl)-glycine, 4-nitrophenyl N-(tert.-butoxycarbonyl)-L-alanine, 2,4,5-trichlorophenyl N-(tert.-butoxycarbonyl)-D-alanine, 4-nitrophenyl N-(tert.-butoxycarbonyl)-L-leucine, 4-nitrophenyl N-(tert.-butoxycarbonyl)-L-valine, 3-methoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethyl dicarbonate, diethyl dicarbonate, di-tert.-butyl dicarbonate, 4-nitrophenyl 2-(pyrazol-1-yl)-ethyl carbonate, 4-nitrophenyl 2-(triazol-1-yl)-ethyl carbonate, (N-oxido-pyrid-2-yl)-methyl 4-nirophenyl carbonate, (N-oxido-pyrid-3-yl)-methyl 4-nitrophenyl carbonate, (N-oxido-pyrid-4-yl)-methyl 4-nitrophenyl carbonate, dimethylcarbamoyl chloride, trichloromethanesulphenyl chloride, dichlorofluoromethanesulphenyl chloride, trifluoromethanesulphenyl chloride, methoxycarbonylsulphenyl chloride, methanesulphonyl chloride, ethanesulphonyl chloride, propane-1-sulphonyl chloride, benzenesulphonyl chloride, 4-toluene-sulphonyl chloride, butane-1-sulphonyl chloride, perfluorobutane-1-sulphonyl fluoride, 4-chlorobutane-1-sulphonyl chloride and dichlorofluoromethanesulphonyl chloride.

The isocyanates (IV) which can be used according to the invention are known. The following may be mentioned as examples:

Methyl isocyanate, ethyl isocyanate, isopropyl isocyanate, n-propyl 3-isocyanatopropionate, methyl 4-isocyanatobutyrate, methyl 6-isocyanatohexanoate, phenyl isocyanate, 4-methoxyphenyl isocyanate and 3-chlorophenyl isocyanate.

the anhydrides (V) which can be used according to the invention are known. The following may be mentioned as examples:

Succinic anhydride, methylsuccinic anhydride, glutaric anhydride, phthalic anhydride and tetrachlorophthalic anhydride.

The reaction of (II) with (III) (method A) is preferably carried out in a diluent, such as dimethylsulphoxide, N,N-dimethylformamide, tetrahydrofuran, sulpholane, dioxan, pyridine or water, or in mixtures of these diluents, t temperatures of 0° C.–140° C., preferably 10° C.–110° C.

The reaction can be carried out under atmospheric pressure as well as under elevated pressure. In general, the reaction is carried out under pressures between about 1 and about 100 bar, preferably between 1 and 10 bar.

All customary inorganic and orgaic acid-binding agents can be used as acid-binding agents. These preferably include the alkali metal hydroxides, alkali metal carbonates, pyridine and tert.-amines, such as triethylamine and 1,4-diazabicyclo[2.2.2]octane.

In carrying out the process according to the invention, 1 to 4 mol, preferably 1 to 1.5 mol of the compound (III) are employed per mol of the compound (II).

The reaction of (II) with (IV) (method B) is preferably carried out in a diluent, such as dioxane, dimethylsulphoxide, N,N-dimethyl formamide or dilute sodium hydroxide solution, or in mixtures of these diluents.

The reaction temperatures can be varied within a substantial range. In general, the reaction is carried out at between about 0° C. and about 100° C., preferably between 5° C. and 50° C.

The reaction can be carried out under atmospheric pressure as well as under elevated pressure. In general, the reaction is carried out under pressures between about 1 and about 100 bar, preferably between 1 and 10 bar.

In carrying out the process according to the invention, 1–5 mol, preferably 1–2 mol, of the compound (IV) are employed per mol of compound (II).

The reaction of (II) with (V) (method C) is carried out in a diluent, such as N,N-dimethylformamide, dioxane, tetrahydrofuran, pyridine or water, or in mixtures of these diluents. The reaction temperatures can be varied within a substantial range. In general, the reaction is carried out at between about 0° and about 140° C., preferably between 10° and 100° C.

The reaction can be carried out under atmospheric pressure as well as under elevated pressure. In general, the reaction is carried out under pressures between about 1 bar and about 100 bar, preferably between 1 and 10 bar.

All customary inorganic and organic acid-binding agents can be used as acid-binding agents. These preferably include the alkali metal hydroxides, alkali metal carbonates, pyridine and tert.-amines, such as triethylamine and 1,4-diazabicyclo[2.2.2]octane.

In carrying out the process according to the invention, 1 to 3 mol, preferably 1 to 1.3 mol, of the compound (V) are employed per mol of the compound (II).

The following may be mentioned individually as new antibacterial active compounds:

7-[4-Formyl-piperazin-1-yl]-1-cyclopropyl-6-fluoro-1,4-dihydro-4-oxo-quinoline-3-carboxylic acid, 7-[4-acetyl-piperazin-1-yl]-1-cyclopropyl-6-fluoro-1,4-dihydro-4-oxo-quinoline-3-carboxylic acid, 7-[4-chloroacetyl-piperazin-1-yl]-1-cyclopropyl-6-fluoro-1,4-dihydro-4-oxo-quinoline-3-carboxylic acid, 7-[4-trifluoromethylthio-acetyl)-piperazin-1-yl]-1-cyclopropyl-6-fluoro-1,4-dihydro-4-oxo-quinoline-3-carboxylic acid, 7-[4-propionyl-piperazin-1-yl]-1-cyclopropyl-6-fluoro-1,4-dihydro-4-oxo-quinoline-3-carboxylic acid, 7-[4-butyryl-piperazin-1-yl]-1-cyclopropyl-6-fluoro-1,4-dihydro-4-oxo-quinolinecarboxylic acid, 7-[4-(4-chlorobutyryl)-piperazin-1-yl]-1-cyclopropyl-6-fluoro-1,4-dihydro-4-oxo-quinoline-3-carboxylic acid, 7-[4-(3-methyl-butyryl)-piperazin-1-yl]-1-cyclopropyl-6-fluoro-1,4-dihydro-4-oxo-quinoline-3-carboxylic acid, 7-[4-(3-methoxypropionyl)-piperazin-1-yl]-1-cyclopropyl-6-fluoro-1,4-dihydro-4-oxo-quinoline-3-carboxylic acid, 7-[4-benzoyl-piperazin-1-yl]-1-cyclopropyl-6-fluoro-1,4-dihydro-4-oxo-quinoline-3-carboxylic acid, 7-[4-(4-nitrobenzoyl)-piperazin-1-yl]-1-cyclopropyl-6-fluoro-1,4-dihydro-4-oxo-quinoline-3-carboxylic acid, 7-[4-(4-aminobenzoyl)-piperazin-1-yl]-1-cyclopropyl-6-fluoro-1,4-dihydro-4-oxo-quinoline-3-carboxylic acid, 7-[4-(3-carboxypropionyl)-piperazin-1-yl]-1-cyclopropyl-6-fluoro-1,4-dihydro-4-oxo-quinoline-3-carboxylic acid, 7-[4-(4-carboxybutyryl)-piperazin-1-yl]-1-cyclopropyl-6-fluoro-1,4-dihydro-4-oxo-quinoline-3-carboxylic acid, 7-[4-(2-carboxybenzoyl)-piperazin-1-yl]-1-cyclopropyl-6-fluoro-1,4-dihydro-4-oxo-quinoline-3-carboxylic acid, 7-[4-(2-carboxy-3,4,5,6-tetrachlorobenzoyl)-piperazin-1-yl]-1-cyclopropyl-6-fluoro-1,4-dihydro-4-oxo-quinoline-3-carboxylic acid, 7-[4-(3-methoxycarbonyl-propionyl-piperazin-1-yl]-1-cyclopropyl-6-fluoro-1,4-dihydro-4-oxo-quinoline-3-carboxylic acid, 7-[4-(hydroxyacetyl)-piperazin-1-yl]-1-cyclopropyl-6-fluoro-1,4-dihydro-4-oxo-quinoline-3-carboxylic acid, 7-[4-(aminoacetyl)-piperazin-1-yl]-1-cyclopropyl-6-fluoro-1,4-dihydro-4-oxo-quinoline-3-carboxylic acid, 7-[4-(2-aminopropionyl)-piperazin-1-yl]-1-cyclopropyl-6-fluoro-1,4-dihydro-4-oxo-quinoline-3-carboxylic acid, 7-[4-(2-amino-3-methyl-butyryl)-piperazin-1-yl]-1-cyclopropyl-6-fluoro-1,4-dihydro-4-oxo-quinoline-3-carboxylic acid, 7-[4-(2-amino-4-methyl-pentanoyl)-piperazin-1-yl]-1-cyclopropyl-6-fluoro-1,4-dihydro-4-oxo-quinoline-3-carboxylic acid, 7-[4-(2-hydroxy-4-amino-butyryl)-piperazin-1-yl]-1-cyclopropyl-6-fluoro-1,4-dihydro-4-oxo-quinoline-3-carboxylic acid, 7-[4-methoxycarbonyl-piperazin-1-yl]-1-cyclopropyl-6-fluoro-1,4-dihydro-4-oxo-quinoline-3-carboxylic acid, 7-[4-ethoxycarbonyl-piperazin-1-yl]-1-cyclopropyl-6-fluoro-1,4-dihydro-4-oxo-quinoline-3-carboxylic acid, 7-[4-n-butoxycarbonyl-piperazin-1-yl]-1-cyclopropyl-6-fluoro-1,4-dihydro-4-oxo-quinoline-3-carboxylic acid, 7-[4-tert.-butoxycarbonyl-piperazin-1-yl]-1-cyclopropyl-6-fluoro-1,4-dihydro-4-oxo-quinoline-3-carboxylic acid, 7-{4-[2-(1-pyrazolyl)-ethoxycarbonyl]-piperazin-1-yl}-1-cyclopropyl-6-fluoro-1,4-dihydro-4-oxo-quinoline-3-carboxylic acid, 7-{4-[2-(1,2,3-triazol-1-yl)-ethoxycarbonyl]-piperazin-1-yl}-1-cyclopropyl-6-fluoro-1,4-dihydro-4-oxo-quinoline-3-carboxylic acid, 7-[4-(2-chloroethyloxycarbonyl)-piperazin-1-yl]-1-cyclopropyl-6-fluoro-1,4-dihydro-4-oxo-quinoline-3-carboxylic acid, 7-{4-[(N-oxide-3-pyridyl)-methyl]-piperazin-1-yl}-1-cyclopropyl-6-fluoro-1,4-dihydro-4-oxo-quinoline-3-carboxylic acid, 7-[4-carbamoyl-piperazin-1-yl]-1-cyclopropyl-6-fluoro-1,4-dihydro-4-oxo-quinoline-3-carboxylic acid, 7-[4-methylcarbamoyl-piperazin-1-yl]-1-cyclopropyl-6-fluoro-1,4-dihydro-4-oxo-quinoline-3-carboxylic acid, 7-[4-hexylcarbamoyl-piperazin-1-yl]-1-cyclopropyl-6-fluoro-1,4-dihydro-4-oxo-quinoline-3-carboxylic acid, 7-[4-phenylcarbamoyl]-1-cyclopropyl-6-fluoro-1,4-dihydro-4-oxo-quinoline-3-carboxylic acid, 7-{4-[(3-methoxycarbonylpropyl)-carbamoyl]-piperazin-1-yl}-1-cyclopropyl-6-fluoro-1,4-dihydro-4-oxo-quinoline-3-carboxylic acid, 7-{4-[(5-methoxycarbonylpentyl)-carbamoyl]-piperazin-1-yl}-1-cyclopropyl-6-fluoro-1,4-dihydro-4-oxo-quinoline-3-carboxylic acid, 7-{4-[(3-carboxypropyl)-carbamoyl]-piperazin-1-yl}-1-cyclopropyl-6-fluoro-1,4-dihydro-4-oxo-quinoline-3-carboxylic acid, 7-{4-[(5-carboxypentyl)-carbamoyl]-piperazin-1-yl}-1-cyclopropyl-6-fluoro-1,4-dihydro-4-oxo-quinoline-3-carboxylic acid, 7-{4-[(2-propoxycarbonyl)-carbamoyl]-piperazin-1-yl}-1-cyclopropyl-6-fluoro-1,4-dihydro-4-oxo-quinoline-3-carboxylic acid, 7-{4-[(2-carboxyethyl)-carbamoyl]-piperazin-1-yl}-1-cyclopropyl-6-fluoro-1,4-dihydro-4-oxo-quinoline-3-carboxylic acid, 7-[4-dimethylcarbamoyl-piperazin-1-yl]-1-cyclopropyl-6-fluoro-1,4-dihydro-4-oxo-quinoline-3-carboxylic acid, 7-{4-[(4-chlorobutyl)-carbamoyl]-piperazin-1-yl}-1-cyclopropyl-6-fluoro-1,4-dihydro-4-oxo-quinoline-3-carboxylic acid 7-[4-cyano-piperazin-1-yl]-1-cyclopropyl-6-fluoro-1,4-dihydro-4-quinoline-carboxylic acid, 7-[4-trichloromethanesulphenyl-piperazin-1-yl]-1-cyclopropyl-6-fluoro-1,4-dihydro-4-oxo-quinoline-3-carboxylic acid, 7-[4-ethoxycarbonylsulphenyl-piperazin-1-yl]-1-cyclopropyl-6-fluoro-1,4-dihydro-4-oxo-quinoline-3-carboxylic acid, 7-[4-methanesulphonyl-piperazin-1-yl]-1-cyclopropyl-6-fluoro-1,4-dihydro-4-oxo-quinoline-3-carboxylic acid, 7-[4-dichloromethanesulphonyl-piperazin-1-yl]-1-cyclopropyl-6-fluoro-1,4-dihydro-4-oxo-quinoline-3-carboxylic acid, 7-[4-n-propanesulphonyl-piperazin-1-yl]-1-cyclopropyl-6-fluoro-1,4-dihydro-4-oxo-quinoline-3-carboxylic acid, 7-[4-(4-chlorobutane-1-sulphonyl)-piperazin-1-yl]-1-cyclopropyl-6-fluoro-1,4-dihydro-4-oxo-quinoline-3-carboxylic acid, 7-[4-perfluorobutane-1-sulphonyl-piperazin-1-yl]-1-cyclopropyl-6-fluoro-1,4-dihydro-4-quinoline-3-carboxylic acid, 7-[4-acetyl-3-methyl-piperazin-1-yl]-1-cyclopropyl-6-fluoro-1,4-dihydro-4-oxo-quinoline-3-carboxylic acid, 7-[3-methyl-4-propionyl-piperazin-1-yl]-1-cyclopropyl-6-fluoro-1,4-dihydro-4-oxo-quinoline-3-carboxylic acid, 7-[3-methyl-4-methylcarbamoyl-piperazin-1-yl]-1-cyclopropyl-6-fluoro-1,4-dihydro-4-oxo-quinoline-3-carboxylic acid, 7-[2,5-dimethyl-4-formyl-piperazin-1-yl]-1-cyclopropyl-6-fluoro-1,4-dihydro-4-oxo-quinoline-3-carboxylic acid, 7-[2,5-dimethyl-4-butyryl-piperazin-1-yl]-1-cyclopropyl-6-fluoro-1,4-dihydro-4-oxo-quinoline-3-carboxylic acid, 7-[3,5-dimethyl-4-acetyl-piperazin-1-yl]-1-cyclopropyl-6-fluoro-1,4-dihydro-4-oxo-quinoline-3-carboxylic acid, 7-[3,5-dimethyl-4-carbamoyl-piperazin-1-yl]-1-cyclopropyl-6-fluoro-1,4-dihydro-4-oxo-quinoline-3-carboxylic acid, 7-(4-butyryl-piperazin-1-yl)-1-cyclopropyl-1,4-dihydro-6-nitro-4-oxo-quinoline-3-carboxylic acid, 7-(4-butyryl-piperazin-1-yl)-6-chloro-1 cyclopropyl-1,4-dihydro-4-oxo-quinoline-3-carboxylic acid, 7-(4-butyryl-piperazin-1-yl)-1-cyclopropyl-1,4-dihydro-4-oxo-quinoline-3-carboxylic acid, 7-[4-(2-aminopropionyl)-3-methyl-piperazin-1-yl]-1-cyclopropyl-6-fluoro-1,4-dihydro-4-oxo-quinoline-3-carboxylic acid and 7-(4-butyryl-3,5-dimethyl-piperazin-1-yl)-1-cyclopropyl-6-fluoro-1,4-dihydro-4-oxo-quinoline-3-carboxylic acid.

The compounds according to the invention, of the formula (I), can, if desired, be converted with an organic or inorganic acid to a salt especially a pharmaceutically acceptable acid addition salt. Examples of acids which are suitable for salt formation are hydrohalic acids, such as hydrochloric acid, hydrobromic acid, hydriodic acid, sulphuric acid, acetic acid, citric acid, ascorbic acid, methanesulphonic acid and benzenesulphonic acid. Preferred alkali metal salts or alkaline earth metal salts are sodium salts, potassium salts, calcium salts and magnesium salts.

The compounds according to the invention exhibit a broad antibacterial spectrum against Gram-positive and Gram-negative organisms, particularly against enterobacteriaceae; in particular even against those which are resistant to a variety of antibiotics, such as, for example, penicillins, cephalosporins, aminoglycosides, sulphonamides and tetracylins.

The compounds according to the invention have low toxicity and a potent and broad antimicrobial efficacy. These properties make it possible to use them as chemotherapeutic active compounds in medicine and as substances for preparing inoranic and organich materials, in particular organic materials of all types, for example polymers, lubricants, dyes, fibres, leather, paper and wood, foodstuffs and water. The compounds according to the invention are active against a very broad spectrum of microorganisms. Using them, Gram-negative and Gram-positive bacteria and bacterioid microorganisms can be controlled and the diseases caused by these pathogens can be treated.

The compounds according to the invention are particularly active against bacteria and bacterioid microorganisms. Thus they are particularly well suited for the chemotherapy of local and systemic infections caused by these pathogens in medicine.

For example, local and/or systemic diseases caused by the following pathogens or by mixtures of the following pathogens can be treated and/or prevented: Micrococcaceae, such as staphylococci, for example Staphylococcus aureus, Staph. Epidermidis, (Staph.=Staphylococcus); Lactobacteriaceae, such as streptococci, for example *Streptococcus pyogenes*, α- and β-haemolytic streptococci, non (γ-) *haemolytic streptococci*, enterococci and *Diplococcus pneumoniae* (pneumococci) (Str.=Streptococcus); Enterobacteriaceae, such as escherichiae bacteria of the coli group: escherichia bacteria, for example *Escherichia coli*, enterobacter bacteria, for example aerogenes, *E. cloacae,* Klebsiella bacteria, for example K. pneumoniae, serratia, for example *Serratia marcescens* (E.=Enterobacter) (K.=Klebsiella), proteae bacteria of the proteus group: proteus, for example *Proteus vulgaris, Pr.morganii, Pr.rettgeri* and *Pr.mirabilis* (Pr.=Proteus); pseudomonadaceae, such as pseudomonas bacteria, for example *Pseudomonas aeruginosa* (PS.=Pseudomonas); bacteroidaceae, such as bacteroides bacteria, for example *Bacteroides fragilis* (B.=Bacteroides); mycoplasma, for example *Mycoplasma pneumonia.*

The above list of pathogens is merely exemplary and should not by any means be interpreted as restrictive.

The following may be mentioned as examples of illness which can be treated by the compounds according to the invention: diseases of the respiratory tract and the pharyngeal cavity: otitis; pharyngitis; pneumonia; peritonitis; pyelonephritis; cystitis; endocarditis; systemic infections; bronchitis; arthritis; local infections and septic diseases.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, dragrees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium metahydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the active compounds according to the invention.

The abovementioned pharmaceutical preparations are manufactured in the usual manner according to known methods, for example by mixing the active compound or the active compounds with the excipient or excipients.

The active compounds or the pharmaceutical preparations can be administered locally, orally, parenterally, intraperitoneally and/or rectally, preferably orally or parenterally, such as intravenously or intramuscularly. In general, it has proved advantageous in medicine to administer the active compound or compounds in total amounts of about 0.5 to about 50, preferably 1 to 30, especially preferably 1–20 mg/kg of body weight, orally or parenterally, every 24 hours, optionally in the form of several individual administrations, in order to achieve the desired results. An individual administration contains the active compound or the active compounds preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of his expert knowledge.

The new compounds can be utilized as feedstuff additives and used in the customary concentrations and preparations together with the feed or with the feed preparations or with the drinking water. By this means, a promotion of growth and an improvement in the utilization of the feed can be achieved. Preparation Examples for the starting compound:

EXAMPLE A

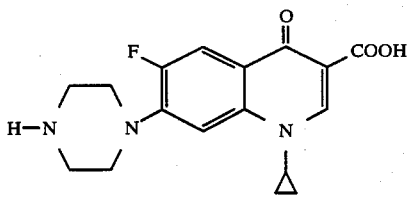

A mixture of 19.7 g of 7-chloro-1-cyclopropyl-6-fluoro-1,4-dihydro-4-oxo-quinoline-3-carboxylic acid, 30.1 g of anhydrous piperazine and 100 ml of dimethyl-sulphoxide is heated for 2 hours at 135°–140° C. The solvent is distilled off in a fine vacuum, and the residue is suspended in $H_2O$, filtered off and washed with water. For further purification, the moist crude product is boiled up with 100 ml of water, filtered off at room temperature, washed with $H_2O$ and dried in a vacuum drying oven over $CaCl_2$ at 100° C. until the weight remains constant. 19.6 g of 1-cyclopropyl-6-fluoro-1,4-dihydro-4-oxo-7-(piperazin-1-yl)-quinoline-3-carboxylic acid which decomposes at 255°–257° C. are obtained.

The 7-chloro-1-cyclopropyl-6-fluoro-1,4-dihydro-4-oxo-quinoline-3-carboxylic acid VIa used as a starting material is prepared as follows:

24.3 g of magnesium turnings are suspended in 50 ml of anhydrous ethanol. 5 ml of carbon tetrachloride are added, and, when the reaction has started, a mixture of 160 g of diethyl malonate, 100 ml of absolute ethanol and 400 ml of anhydrous ether is added dropwise, vigorous refluxing taking place. After the reaction has died down, the mixture is heated at the boil for a further 2 hours and cooled to $-5°$ C. to $-10°$ C. with dry ice-/acetone, and a solution of 227.5 g of 2,4-dichloro-5-fluoro-benzoyl chloride (1) in 100 ml of absolute ether is slowly added dropwise at this temperature. The mixture is stirred for 1 hour at 0° C. to $-5°$ C., and is allowed to reach room temperature overnight, and a mixture of 400 ml of ice water and 25 ml of concentrated sulphuric acid is allowed to run in, while cooling with ice. The phases are separated, and further extracted twice with ether. The combined ether solutions are washed with saturated NaCl solution and dried with $Na_2SO_4$, and the solvent is stripped off in vacuo. 349.5 g of diethyl 2,4-dichloro-5-fluoro-benzoyl-malonate (3) are obtained as a crude product.

0.15 g of p-toluenesulphonic acid is added to an emulsion of 34.9 g of crude diethyl 2,4-dichloro-5-fluoro-benzoyl-malonate (3) in 50 ml of water. The thoroughly stirred mixture is heated at the boil for 3 hours, the cooled emulsion is extracted several times with methylene chloride, the combined $CH_2Cl_2$ solutions are washed once with saturated NaCl solution and dried with $Na_2SO_4$, and the solvent is distilled off in vacuo. Fractionation of the residue in vacuo gives 21.8 g of ethyl 2,4-dichloro-5-fluoro-benzoyl-acetate (4) of boiling point 127°–142° C./0.09 mbar.

A mixture of 21.1 g of ethyl 2,4-dichloro-5-fluoro-benzoyl-acetate (4), 16.65 g of ethyl o-formate and 18.55 g of acetic anhydride is heated to 150° C. for 2 hours. Thereafter, the volatile components are distilled off in the vacuum from a waterpump and finally in a fine vacuum, at a bath temperature of 120° C. 35.2 g of crude ethyl 2-(2,4-dichloro-5-benzoyl)-3-ethoxy-acrylate (5) remain. It is sufficiently pure for the further reactions.

4.3 g of cyclopropylamine are added dropwise to a stirred ice-cooled solution of 24.9 g of ethyl 2-(2,4-dichloro-5-fluoro-benzoyl)-3-ethoxy-acrylate (5) in 80 ml of ethanol. When the exothermic reaction has died down, stirring is continued for a further hour at room temperature, the solvent is stripped off in vacuo and the residue is recrystallised from cyclohexane/petroleum ether. 22.9 g of ethyl 2-(2,4-dichloro-5-fluoro-benzoyl)-3-cyclopropylamino-acrylate (6) of melting point 89°–90° C. are obtained.

3.44 g of 80 percent strength sodium hydride are added in portions to a stirred ice-cooled solution of 31.9 g of ethyl 2-(2,4-dichloro-5-fluoro-benzoyl)-3-cyclopropylamino-acrylate (6) in 100 ml of anhydrous dioxane. Thereafter, the mixture is stirred for 30 minutes at room temperature and for 2 hours under reflux, and the dioxane is stripped off in vacuo. The residue (40.3 g) is suspended in 150 ml of water, 6.65 g of caustic alkali are added and the mixture is refluxed for 1.5 hours. The warm solution is filtered, and the residue is rinsed with $H_2O$. The ice-cooled filtrate is then acidified to $pH=1-2$ with semi-concentrated hydrochloric acid, and the precipitate is filtered off under suction, washed with water and dried in vacuo at 100° C. In this manner, 27.7 g of 7-chloro-1-cyclopropyl-6-fluoro-1,4-dihydro-4-oxo-quinoline-3-carboxylic acid Via of melting point 234°–237° C. are obtained.

EXAMPLE B

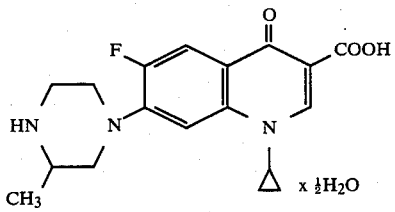

A mixture of 2.8 g (0.01 mol) of 7-chloro-1-cyclopropyl-6-fluoro-1,4-dihydro-4-oxo-quinoline-3-carboxylic acid and 5.1 g (0.051 mol) of 2-methylpiperazine in 6 ml of dimethylsulphoxide is heated to 140° C. for 2 hours. Thereafter, the solvent is distilled off in a high vacuum, 6 ml of hot water are added to the residue, and the mixture is kept at 95° C. for 1 hour. The mixture is cooled with ice, and the precipitate which separates out is filtered off under suction, washed with a little water and dissolved in a mixture of 0.8 ml of acetic acid and 10 ml of water at 90°–100° C. The filtrate is brought to pH 8 with potassium hydroxide solution (0.75 g of KOH in 0.7 ml of water), and the precipitate which separates out is recrystallised from methanol. 4.8 g (52% of theory) of 1-cyclopropyl-6-fluoro-1,4-dihydro-4-oxo-7-(3-methyl-piperazin-1-yl)-quinoline-3-carboxylic acid semihydrate which decomposes at 230°–232° C. are obtained.

EXAMPLE C

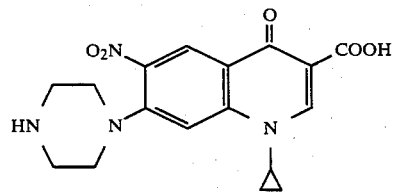

A mixture of 9.3 g (0.03 mol) of 7-chloro-1-cyclopropyl-1,4-dihydro-6-nitro-4-oxo-quinoline-3-carboxylic acid and 12.9 g (0.15 mol) of piperazine in 60 ml of dimethylsulphoxide is heated to 120° C. for 15 minutes. After a short time, a precipitate separates out from the hot solution. The mixture is evaporated down in a high vacuum, stirred with 30 ml of water and heated to 95° C. for a further 30 minutes. The mixture is adjusted to pH 8 with 2N hydrochloric acid, and the precipitate is filtered off under suction and washed with water and methanol. 5.8 g (54% of theory) of 1-cyclopropyl-1,4-dihydro-6-nitro-4-oxo-7-(piperazin-1-yl)-quinoline-3-carboxylic acid which decomposes at 296°–298° C. are isolated.

EXAMPLE D

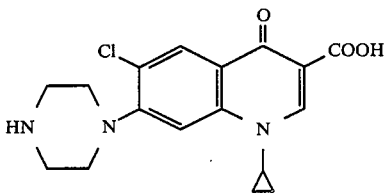

Analogously to Example C, 6,7-dichloro-1-cyclopropyl-1,4-dihydro-4-oxo-quinoline-3-carboxylic acid is converted to 1-cyclopropyl-6-chloro-1,4-dihydro-4-oxo-7-(piperain-1-yl)-quinoline-3-carboxylic acid which decomposes at 295°–298° C.

EXAMPLE E

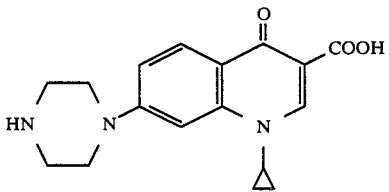

Analogously to Example C, 7-chloro-1-cyclopropyl-1,4-dihydro-4-oxo-quinoline-3-carboxylic acid is reacted with piperazine to give 1-cyclopropyl-1,4-dihydro-4-oxo-7-(piperazin-1-yl)-quinoline-3-carboxylic acid which decomposes at 298°–300° C. Preparation Examples for the end products according to the invention:

EXAMPLE 1

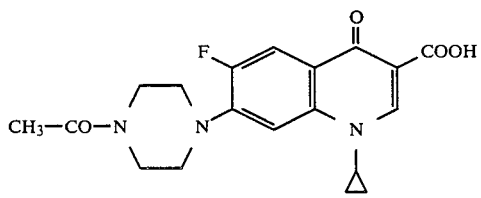

3.3 g (0.01 mol) of 1-cyclopropyl-6-fluoro-1,4-dihydro-4-oxo-7-(piperazin-1-yl)-quinoline-3-carboxylic acid are dissolved in a mixture of 20 ml of dioxane and a solution of 0.4 g of sodium hydroxide in 5 ml of water. A solution of 0.9 g (0.011 mol) of acetyl chloride in 5 ml of dioxane and a solution of 0.4 g (0.01 mol) of sodium hydroxide in 5 ml of water are simultaneously added dropwise to this mixture while cooling with ice, the pH value being kept >8. Stirring is continued for 2 hours at room temperature, 30 ml of water are added to the suspension, the mixture is acidified with 2N hydrochloric acid and the precipitate is filtered off under suction and recrystallised from glycol monomethyl ether. 2 g (54% of theory) of 7-(4-acetyl-piperazin-1-yl)-1-cyclopropyl-6-fluoro-1,4-dihydro-4-oxo-quinoline-3-carboxylic acid which decomposes at 267°–270° C. are isolated.

The following compounds are obtained similarly to Example 1:

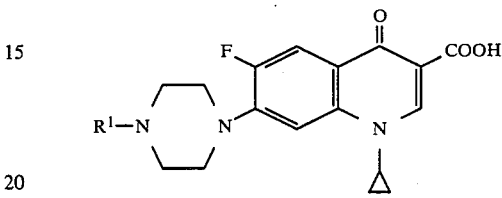

| Example | R$^1$ | Melting point °C. |
|---|---|---|
| 2 | CH$_3$CH$_2$—CO | 267 (decomposition) |
| 3 | CH$_3$CH$_2$CH$_2$—CO | 282 (decomposition) |
| 4 | CH$_3$\\CH—CH$_2$—CO / CH$_3$ | 286 (decomposition) |
| 5 | CF$_3$—S—CH$_2$—CO | 252 (decomposition) |
| 6 | C$_6$H$_5$—CO | 324 (decomposition) |
| 7 | CH$_3$O—CO—CH$_2$CH$_2$—CO | 205 |
| 8 | CN | 276 (decomposition) |
| 9 | CH$_3$O—CO | 270 (decomposition) |
| 10 | C$_2$H$_5$OCO | 315 (decomposition) |
| 11 | n-C$_4$H$_9$OCO | 245 |
| 12 | C$_6$H$_5$—CH$_2$O—CO | 230 |
| 12a | C$_2$H$_5$—S—CO | 322 (decomposition) |
| 13 | CH$_3$—SO$_2$ | 305 (decomposition) |
| 14 | n-C$_3$H$_7$—SO$_2$ | 268 (decomposition) |
| 15 | CFCl$_2$—SO$_2$ | 278 (decomposition) |
| 16 | CCl$_3$—S | 172 (decomposition) |
| 17 | CFCl$_2$—S | 188 (decomposition) |
| 18 | CH$_3$O—CO—S | 204 (decomposition) |
| 19 | CH$_3$CH$_2$CH$_2$—O—CH$_2$—CO | 220 |

EXAMPLE 20

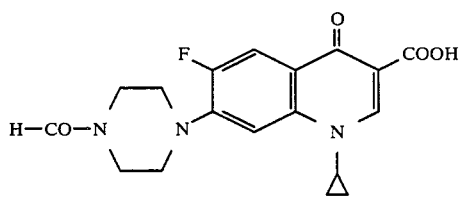

The procedure described in Example 1 is followed, formic acetic anhydride is used, and 1-cyclopropyl-6-fluoro-7-(4-formyl-piperazin-1-yl)-1,4-dihydro-4-oxo-quinoline-3-carboxylic acid which decomposes at 278°–281° C. is obtained.

EXAMPLE 21

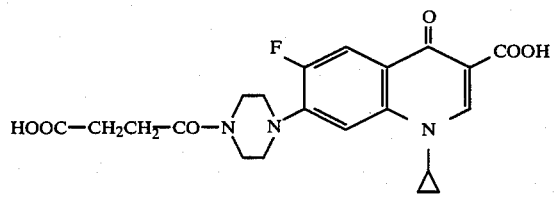

3.3 g (0.01 mol) of 1-cyclopropyl-6-fluoro-1,4-dihydro-4-oxo-7-(piperazin-1-yl)-quinoline-3-carboxylic acid are dissolved in a solution of 0.4 g of sodium hydroxide in 20 ml of water, and a solution of 1 g of succinic anhydride in 10 ml of dioxane and 0.4 g of sodium hydroxide in 10 ml of water are added simultaneously at room temperature. Stirring is continued for 2 hours at room temperature, the mixture is acidified with 2N hydrochloric acid, and the precipitate which separates out is filtered off under suction and washed with water and methanol. 3.4 g (79% of theory) of 7-[4-(3-carboxy-propionyl)-piperazin-1-yl]-1-cyclopropyl-6-fluoro-1,4-dihydro-4-oxo-quinoline-3-carboxylic acid which decomposes at 284°–286° C. are obtained.

The following compounds are obtained similarly to Example 21:

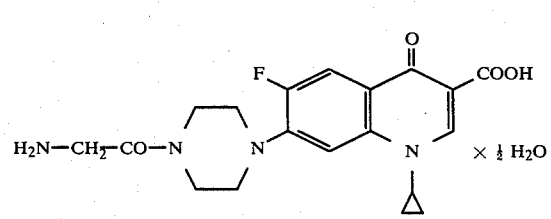

| Example | R¹ | Melting point °C. |
|---|---|---|
| 22 | HOOC—CH₂CH₂CH₂—CO— | 273 |
| 23 | ![Cl-substituted benzoyl with COOH] | 253 (decomposition) |

EXAMPLE 24

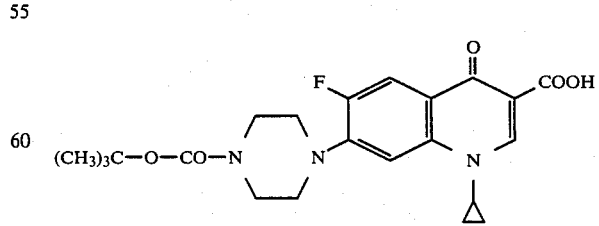

3 g of 4-nitro-phenyl N-(tert.-butoxycarbonyl)-glycine are added to 3.3 g (0.01 mol) of 1-cyclopropyl-6-fluoro-1,4-dihydro-4-oxo-(piperazin-1-yl)-quinoline-3-carboxylic acid in 50 ml of pyridine, and the mixture is stirred for 4 hours at room temperature. The solution is evaporated down, 30 ml of water are added and the pH is adjusted to 5 with 2N hydrochloric acid. The precipitate which separates out is filtered off under suction, washed with water and methanol and dried. 2.7 g (55% of theory) of 7-[4-(tert.-butoxycarbonylamino-acetyl)-piperazin-1-yl]-1-cyclopropyl-6-fluoro-1,4-dihydro-4-oxo-quinoline-3-carboxylic acid which decomposes at 236°–238° C. are obtained. 10 ml of concentrated hydrochloric acid are added to a suspension of 2.2 g (0.0045 mol) of this intermediate product in 100 ml of methanol, and the mixture is left to stand for 3 hours at room temperature. Thereafter, methanol and excess hydrogen chloride are stripped off in vacuo, the aqueous solution is adjusted to pH 8 with dilute sodium hydroxide solution, and the precipitate is filtered off under suction and washed with methanol. 1.4 g (78% of theory) of 7-(aminoacetyl)-1-cyclopropyl-6-fluoro-1,4-dihydro-4-oxo-quinoline-3-carboxylic acid semihydrate which decomposes at 245°–248° C. are obtained.

The following compounds are prepared analogously to Example 24:

| Example | R¹ | Decomposition point °C. |
|---|---|---|
| 25 | C₆H₅—CH(NH₂)—CO— × HCl × H₂O | 297 |
| 26 | CH₃—CH(NH₂)—CO— | 240 |
| 27 | (CH₃)₂CH—CH(NH₂)—CO— × HCl | 280 |
| 28 | H₂N—CH₂—CH₂—CO— × HCl | 274 |

EXAMPLE 29

6 g of di-tert.-butyl pyrocarbonate are added to a solution of 8.25 g (0.025 mol) of 1-cyclopropyl-6-fluoro-1,4-dihydro-4-oxo-7-(piperazin-1-yl)-quinoline-3-carboxylic acid in 75 ml of dioxane/water (2:1) and 25 ml of 1N sodium hydroxide solution, while cooling with ice, and the mixture is then stirred for 30 minutes at room temperature. The mixture is evaporated down to one third of its volume, is covered with a layer of 50 ml of ethyl acetate and is acidified to pH 3 with dilute potassium bisulphate solution. The precipitate which separates out is filtered off under suction, washed with water and methanol and dried in a high vacuum. 10 g (92% of theory) of 7-(4-tert.-butoxycarbonyl-piperazin-1-yl)-1-cyclopropyl-6-fluoro-1,4-dihydro-4-oxo-quinoline-3-carboxylic acid which decomposes at 249°–252° C. are obtained.

EXAMPLE 30

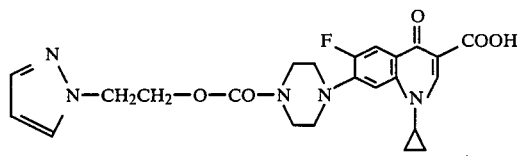

A mixture of 3.3 g (0.01 mol) of 1-cyclopropyl-6-fluoro-1,4-dihydro-4-oxo-7-(piperazin-1-yl)-quinoline-3-carboxylic acid and 2.8 g (0.01 mol) of 4-nitrophenyl 2-(pyrazol-1-yl)-ethyl carbonate in 40 ml of pyridine is stirred for 1 day at room temperature. Thereafter, it is diluted with 30 ml of water and acidified with 2N hydrochloric acid, and the precipitate is filtered off under suction and recrystallised from glycol monomethyl ether. 2.8 g (60% of theory) of 1-cyclopropyl-6-fluoro-1,4-dihydro-4-oxo-7-{-4-[(pyrazol-1-yl)-ethoxycarbonyl]-piperazin-1-yl}-quinoline-3-carboxylic acid of melting point 205°–208° C. are obtained.

The 4-nitrophenyl 2-(pyrazol-1-yl)-ethyl carbonate employed as a starting material is obtained by the following route: 4.6 g of 1-(2-hydroxyethyl)-pyrazole in 80 ml of acetonitrile are stirred with 4 g of 4-nitrophenyl chlorocarbonate at room temperature for 12 hours, the solution is evaporated down, the oil obtained is taken up in methylene chloride and the solution is washed with water. It is dried with sodium sulphate and evaporated down, and the crude carbonate is obtained as a viscous oil.

The following compounds are obtained analogously to Example 30:

| Example | R | Melting point °C. |
|---------|---|-------------------|
| 31 | ![pyrazole-CH2CH2] | 226 |
| 32 | ![pyridine-CH2 with O] | 236 (decomposition) |
| 33 | ![pyridine-CH2 with O] | 203 (decomposition) |

EXAMPLE 34

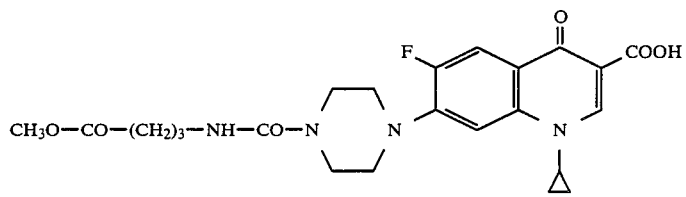

6.6 g (0.02 mol) of 1-cyclopropyl-6-fluoro-1,4-dihydro-4-oxo-7-(piperazin-1-yl)-quinoline-3-carboxylic acid are dissolved in a solution of 0.4 g of sodium hydroxide in 40 ml of water, and a solution of 3.2 g (0.022 mol) of methyl 4-isocyanato-butyrate in 12 ml of dioxane is added, while cooling with ice. Thereafter, stirring is continued for 2 hours at room temperature, the pH is adjusted to 5 with 2N hydrochloric acid and the precipitate is filtered off under suction and recrystallised from methanol. 6 g (63% of theory) of 1-cyclopropyl-6-fluoro-1,4-dihydro-4-oxo-7-{4-[(3-methoxycarbonylpropyl)-carbamoyl]-piperazin-1-yl}-quinoline-3-carboxylic acid of melting point 198°–200° C. are obtained.

The following compounds are obtained similarly to Example 34:

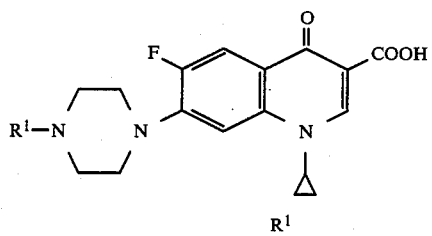

| Example | R¹ | Melting point (°C.) |
|---|---|---|
| 35 | CH₃O—CO(CH₂)₅—NH—CO | 178 |
| 36 | C₃H₇O—CO—(CH₂)₂—NH—CO | 180 (decomp.) |
| 37 | CH₃—NH—CO | 280 (decomp.) |

EXAMPLE 38

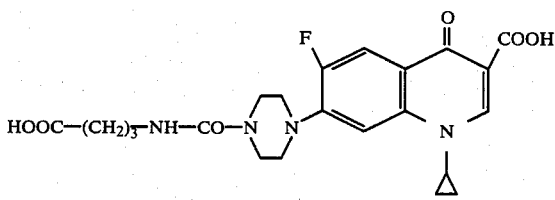

2.37 g of the compound of Example 34 in a mixture of 10 ml of glacial acetic acid, 6.5 ml of water and 1 ml of concentrated sulphuric acid are heated to 150°–160° C. for 1.5 hours. After cooling to room temperature, the mixture is poured onto 50 ml of ice water, and the precipitate is filtered off under suction and recrystallised from glycol monomethyl ether. 1.2 g (52% of theory) of 7-{4-[(3-carboxyl-propyl)-carbamoyl]-piperazin-1-yl}-1-cyclopropyl-6-fluoro-1,4-dihydro-4-oxo-quinoline-3-carboxylic acid which decomposes at 245°–248° C. are isolated.

The following compounds are obtained similarly to Example 38, by hydrolysis of the products from Examples 35 and 36:

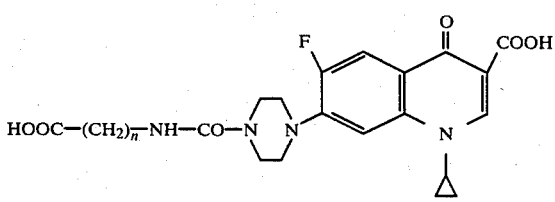

| Example | n | Melting point (°C.) |
|---|---|---|
| 39 | 5 | 224 (decomposition) |
| 40 | 2 | 209 (decomposition) |

EXAMPLE 41

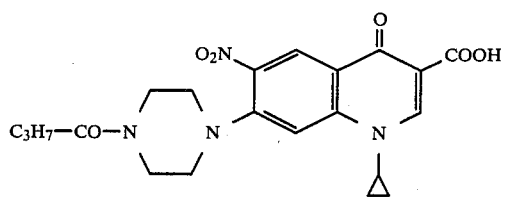

Using a method similar to that of Example 1, 1-cyclopropyl-1,4-dihydro-6-nitro-4-oxo-7-(piperazin-1-yl)-quinoline-3-carboxylic acid and butyryl chloride are converted to 7-(4-butyryl-piperazin-1-yl)-1-cyclopropyl-1,4-dihydro-6-nitro-4-oxo-quinoline-3-carboxylic acid which decomposes at 223°–226° C.

EXAMPLE 42

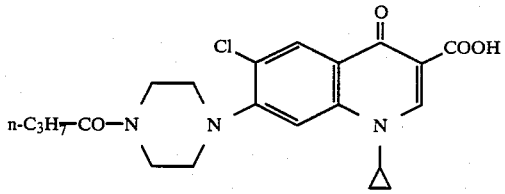

Using a method similar to that described in Example 1, 6-chloro-1-cyclopropyl-1,4-dihydro-4-oxo-7-(piperazin-1-yl)-quinoline-3-carboxylic acid and butyryl chloride are converted to 7-(4-butyryl-piperazin-1-yl)-6-chloro-1-cyclopropyl-1,4-dihydro-4-oxo-quinoline-3-carboxylic acid which decomposes at 280°–283° C.

EXAMPLE 43

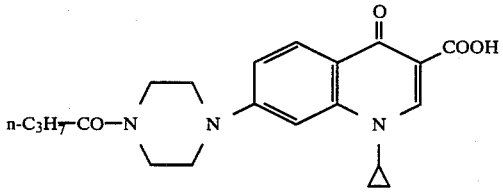

Using a method similar to that described in Example 1, 1-cyclopropyl-1,4-dihydro-4-oxo-7-(piperazin-1-yl)-quinoline-3-carboxylic acid and butyryl chloride are converted to 7-(4-butyryl-piperazin-1-yl)-1-cyclopropyl-1,4-dihydro-4-oxo-quinoline-3-carboxylic acid which decomposes at 252°–255° C.

EXAMPLE 44

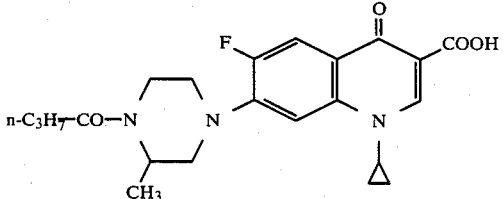

Using a method similar to that described in Example 1, 1-cyclopropyl-6-fluoro-1,4-dihydro-4-oxo-7-(3-methylpiperazin-1-yl)-quinoline-3-carboxylic acid and butyryl chloride are converted to 7-(4-butyryl-3-methyl-piperazin-1-yl)-1-cyclopropyl-6-fluoro-1,4-dihydro-4-oxo-quinoline-3-carboxylic acid which decomposes at 226°–228° C.

The compounds according to the invention have good actions against gram positive and gram negative bacteria. In the table below, the minimum inhibitory concentrations for compounds according to the invention are given for a few bacteria. They were obtained in the agar dilution test with the aid of a multi-point inoculator (Denley) on Isosensitest agar in the Case of Example 20, and by means of the agar incorporation test on DST medium in the case of Examples 17, 21 and 15.

| Strain | Example 17 | Example 21 | Example 20 | Example 15 |
|---|---|---|---|---|
| E. coli Neumann | 0.03 | 0.06 | | 0.03 |
| Klebs. 8085 | 0.125 | | | 0.125 |
| Proteus 1017 | 0.03 | 0.06 | | 0.03 |
| Pseudom. W. | 0.5 | | | 0.5 |
| Staph. 133 | | 2 | 0.25 | 1 |

We claim:

1. A quinolonecarboxylic acid of the formula (I)

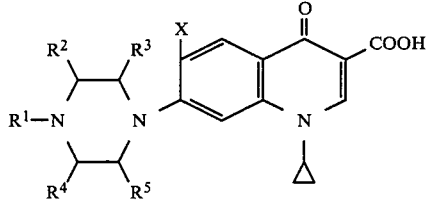

in which

R$^1$ denotes CO—R$^6$, CN, SO$_2$—R$^7$, S—R$^8$,

R$^6$ denotes hydrogen, straight-chain or branched alkyl which has 1 to 5 C atoms and is optionally substituted by 1 to 3 substituents selected from the group from the series consisting of amino, chlorine, alkoxycarbonyl having 1 to 4 carbon atoms in the alkyl part, carboxyl, alkoxy having 1 to 4 carbon atoms, hydroxyl and trifluoromethylthio, phenyl which is optionally substituted by 1 to 5 substituents selected from the group consisting of fluorine, chlorine, hydroxyl, methoxy, amino and carboxyl, benzyl which is optionally substituted by amino, alkoxy or alkylthio which has 1 to 5 C atoms and is optionally substituted by fluorine, chlorine, pyrazol-1-yl, 1,2,3-triazol-1-yl or N-oxido-2-, -3- or -4-pyridyl-methyl, benzyloxy, amino, alkylamino which has 1 to 5 C atoms and is optionally substituted by alkoxycarbonyl having 1 to 3 C atoms in the alkyl part or by benzyloxycarbonyl or carboxyl, or phenylamino, R$^7$ denotes straight-chain or branched alkyl which has 1 to 4 C atoms and is optionally substituted by 1 to 3 substituents selected from the group consisting of fluorine and amino, or phenyl or methylphenyl, R$^8$ denotes methoxycarbonyl, trichloromethyl or dichlorofluoromethyl, R$^2$, R$^3$, R$^4$ and R$^5$ denote hydrogen, methyl or ethyl and X denotes hydrogen, fluorine, chlorine or nitro or a pharmaceutically usable acid addition salts, alkali metal salt or alkaline earth metal salt of hydrate thereof.

2. A quinolonecarboxylic acid of the formula (I), in claim 1, in which

R$^1$ denotes CO—R$^6$, CN, SO$_2$R$^7$, S—R$^8$,

R$^6$ denotes hydrogen, straight-chain or branched alkyl which has 1 to 4 C atoms and which is optionally substituted by 1 or 2 substituents selected from the group consisting of amino, alkoxycarbonyl having 1 to 3 carbon atoms in the alkyl part, carboxyl, alkoxy having 1 to 3 carbon atoms and trifluoromethylthio, phenyl which is optionally substituted by 1 to 5 substituents selected from the group consisting of chlorine, hydroxyl, amino and carboxyl, benzyl which is optionally substituted by amino, alkoxy which has 1 to 4 C atoms and is optionally substituted by pyrazol-1-yl, 1,2,3-triazol-1-yl, N-oxido-2-, -3- or -4-pyridylmethyl, alkylthio having 1 to 2 C atoms, benzyloxy, amino, or alkylamino which has 1 to 5 C atoms and is optionally substituted by alkoxycarbonyl having 1 to 3 C atoms in the alkyl part or by carboxyl, R$^7$ denotes straight-chain or branched alkyl having 1 to 3 C atoms, phenyl or methylphenyl, R$^8$ denotes methoxycarbonyl, trichloromethyl or dichlorofluoromethyl, R$^2$ denotes hydrogen, methyl or ethyl, R$^3$ denotes hydrogen, R$^4$ denotes hydrogen or methyl, R$^5$ denotes hydrogen and X denotes hydrogen, fluorine, chlorine or nitro.

3. A compound of the formula (I) in claim 1, which is 7-[4-(dichlorofluoromethylsulphonyl)-piperazine-1-yl]-1-cyclopropyl-6-fluoro-1,4-dihydro-4-oxo-quinoline-3-carboxylic acid.

4. A compound of the formula (I) in claim 1, which is 7-[4-dichlorofluoromethylsulphenyl)-piperazine-1-yl]-cyclopropyl-6-fluoro-1,4-dihydro-4-oxo-quinoline-3-carboxylic acid.

5. A compound of the formula (I) in claim 1, which is 1-cyclopropyl-6-fluoro-7-(4-formyl-piperazin-1-yl)-1,4-dihydro-4-oxo-quinoline-3-carboxylic acid.

6. A compound of the formula (I) in claim 1, which is 7-[4-3-carboxypropionyl)-piperazin-1-yl]-1-cyclopropyl-6-fluoro-1,4-dihydro-4-oxo-quinoline-3-carboxylic acid.

7. A compound of the formula (I) in claim 1, which is 7-(4-cyano-piperazin-1-yl)-1-yl)-1-cyclopropyl-6-fluoro-1,4-dihydro-4-oxo-quinoline-3-carboxylic acid.

8. A compound of the formula (I) in claim 1, which is 7-(4-methylsulfonyl-piperazin-1-yl)-1-cyclopropyl-6-fluoro-1,4-dihydro-4-oxo-quinoline-3-carboxylic acid.

9. A pharmaceutical composition containing, as an active ingredient, an antibacterially effective amount of a compound according to claim 1 in admixture with an inert pharmaceutical carrier.

10. A pharmaceutical composition containing, as an active ingredient, an antibacterially effective amount of a compound according to claim 1 in the form of sterile or physiologically isotonic aqueous solution.

11. A composition according to claim 9 containing from 0.5 to 90% by weight of the said active ingredient.

12. A medicament in dosage unit form comprising an antibacterially effective amount of a compound according to claim 2 and an inert pharmaceutical carrier.

13. A medicament of claim 12 in the form of tablets, pills, dragees, capsules, ampules or suppositories.

14. A method of combating bacterial infection in warm-blooded animals which comprises administering to said animals an antibacterially effective amount of a compound according to claim 1 either alone or in admixture with a diluent or in the form of a medicament.

15. A method according to claim 14 in which the active compound is administered orally or parenterally.

* * * * *